(12) United States Patent
Anderson

(10) Patent No.: US 11,883,070 B2
(45) Date of Patent: Jan. 30, 2024

(54) NEEDLE REMOVAL DEVICE FOR INTRAOSSEOUS INFUSION

(71) Applicant: Erick Anderson, Crystal, MN (US)

(72) Inventor: Erick Anderson, Crystal, MN (US)

( * ) Notice: Subject to any disclaimer, the term of this patent is extended or adjusted under 35 U.S.C. 154(b) by 0 days.

(21) Appl. No.: 17/229,589

(22) Filed: Apr. 13, 2021

(65) Prior Publication Data
US 2022/0323110 A1 Oct. 13, 2022

(51) Int. Cl.
*A61B 17/34* (2006.01)

(52) U.S. Cl.
CPC ...... *A61B 17/3468* (2013.01); *A61B 17/3472* (2013.01); *A61B 17/3496* (2013.01)

(58) Field of Classification Search
CPC ............ A61B 17/3468; A61B 17/3472; A61B 17/3496; A61B 17/88; A61B 17/8872; A61M 2005/1583; A61M 2005/1585; A61M 2005/2073; A61M 2005/3247
See application file for complete search history.

(56) References Cited

U.S. PATENT DOCUMENTS

| | | | | |
|---|---|---|---|---|
| 4,842,586 A * | 6/1989 | Hogan | ................. | A61B 50/362 604/198 |
| 4,932,947 A * | 6/1990 | Cardwell | ............ | A61M 5/3257 604/263 |
| 4,969,870 A | 11/1990 | Kramer et al. | | |
| 5,030,206 A * | 7/1991 | Lander | ............... | A61B 17/3496 604/164.12 |
| 5,116,326 A * | 5/1992 | Schmidt | .............. | A61M 5/3243 604/263 |
| 5,135,510 A * | 8/1992 | Maszkiewicz | ...... | A61M 5/3271 604/198 |
| 5,273,541 A * | 12/1993 | Malenchek | ........... | A61M 5/326 604/110 |
| 5,312,364 A | 5/1994 | Jacobs | | |
| 5,476,452 A * | 12/1995 | Thompson | ........ | A61M 39/0208 128/919 |
| 5,713,871 A * | 2/1998 | Stock | .................. | A61M 5/3257 604/263 |
| 5,868,711 A | 2/1999 | Kramer et al. | | |
| 6,395,007 B1 * | 5/2002 | Bhatnagar | .......... | A61B 17/8833 606/86 R |
| 7,699,807 B2 * | 4/2010 | Faust | ................. | A61B 5/14503 604/157 |
| 2005/0248940 A1 | 7/2005 | Miller | | |
| 2005/0261693 A1 | 11/2005 | Miller et al. | | |
| 2006/0015066 A1 | 1/2006 | Turieo et al. | | |
| 2018/0325548 A1 * | 11/2018 | Haverkost | .......... | A61B 17/3423 |
| 2019/0125404 A1 * | 5/2019 | Shippert | .............. | A61B 10/025 |
| 2019/0254707 A1 * | 8/2019 | Virden | ................ | A61M 31/007 |

FOREIGN PATENT DOCUMENTS

WO WO2020012051 A1 1/2020

* cited by examiner

*Primary Examiner* — Larry E Waggle, Jr.
(74) *Attorney, Agent, or Firm* — Mitchell Hamline IP Clinic

(57) ABSTRACT

An intraosseous device may include a chamber portion having a proximal end and a distal end, wherein the proximal end includes a base, a tensile puller configured to extend through the chamber portion and slidingly engage the base, the tensile puller comprising a proximal end and a distal end, an actuator on the proximal end of the tensile puller, and a connector on the distal end of the tensile puller adapted to engage a needle.

20 Claims, 15 Drawing Sheets

NEEDLE REMOVAL DEVICE FOR INTRAOSSEOUS INFUSION

FIELD

The present disclosure pertains to devices and methods for intraosseous infusion.

BACKGROUND

Intraosseous (IO) infusion is achieved by a needle inserted directly into the marrow of a bone. For example, the needle may be inserted into the tibia, femur, humerus, or sternum. IO infusion may be relied upon in emergency situations by first responders or emergency room professionals.

IO infusion devices generally include a needle or cannula. The needle/cannula can be affixed to an insertion device (e.g., a drill) via a threaded connection and can be inserted into the bone by the insertion device. This device may use momentum or rotational force to rapidly puncture the bone. The threaded connection of the needle/cannula may be one of several universal threaded connections that allow the needle, once inserted, to pair to a supply device that delivers fluid into the bone through the needle.

After fluid delivery, the IO needle may be extracted from the bone. Existing methods to extract an IO needle from a bone typically include affixing a standard medical syringe to the IO needle via the threaded connection and, using the syringe as a sort of handle, yanking the needle from the bone. Existing methods fail to conform to modern medical procedure in a way that facilitates a controlled, safe removal. Further, they are not adapted to enable individuals of varying strength across multiple professions to perform the extraction.

BRIEF SUMMARY

An intraosseous device may comprise a receiving portion having a proximal end and a distal end and defining a needle chamber, the receiving portion having a base arranged on the proximal end, a tensile puller configured for articulating within the chamber and extending through and slidingly engaging the base, the tensile puller comprising a proximal end and distal end, wherein the tensile puller is configured to articulate through a lumen of the base, an actuator on the proximal end of the tensile puller, and a connector on the distal end of the tensile puller adapted to engage the distal end of a needle. The chamber may be comprised of a first surface including a first aperture, a second surface including a second aperture, and a sidewall connecting the first surface to the second surface. The tensile puller may be configured to rotate independently from the chamber and can be held by friction of a seal around the tensile puller in the second aperture. The tensile puller may configured to alternate between a deployed position wherein the tensile puller is positioned such that the fitting is at least partially within the second aperture, and a retracted position wherein the tensile puller is positioned such that the fitting and the needle are entirely enclosed by the sidewalls of the container. The chamber may fully contain the needle when the tensile puller is in the retracted position. The device may comprise an engaging means for connecting the tensile puller to the needle. The device may comprise one or more safety locks to prevent the tensile puller from being accidentally moved to the deployed position while in the retracted position. The device may be configured to provide a distribution of forces where a force of the actuation of the tensile puller is between the device and a patient body. The device may be configured to provide a distribution of forces where a weight of a limb opposes the force of actuation of the tensile puller. The device may be configured to provide a distribution of forces where minimal pressure is needed against the patient body to oppose the force of the actuation of the tensile puller. The first surface may be constructed of a material suitable for contacting skin. The first surface may comprise a small surface area with a bullnose shape adapted to contact various points of the patient body. The sidewall may be shaped ergonomically to being held securely. The first surface and sidewall may be removably connected by a threading to the second surface of the chamber for disassembly.

A method for extracting an intraosseous needle from a patient may comprise providing or obtaining a medical device comprising a chamber, a tensile puller, an actuator, and a connector, coupling a needle to the connector on a distal end of the tensile puller, applying a force to the chamber towards a distal end of the chamber and until the distal end of the chamber contacts a patient body, and applying a force to the actuator on a proximal end of the tensile puller such that the tensile puller has a force against the patient body, the force effectively altering the tensile puller from a deployed position to a retracted position. The method may comprise engaging one or more safety locks to prevent the tensile puller from moving from the retracted position back to the deployed position. Minimal rotational force from the tensile puller may be required during extraction. Minimal force of pressure on the patient body may be required to oppose the force to an actuator during extraction. The method may comprise disposing of the needle, disposing comprising disassembly of the chamber, decoupling the needle from the connector at the distal end of the tensile puller; and autoclaving of the device for subsequent use.

DETAILED DESCRIPTION

Figure 1:
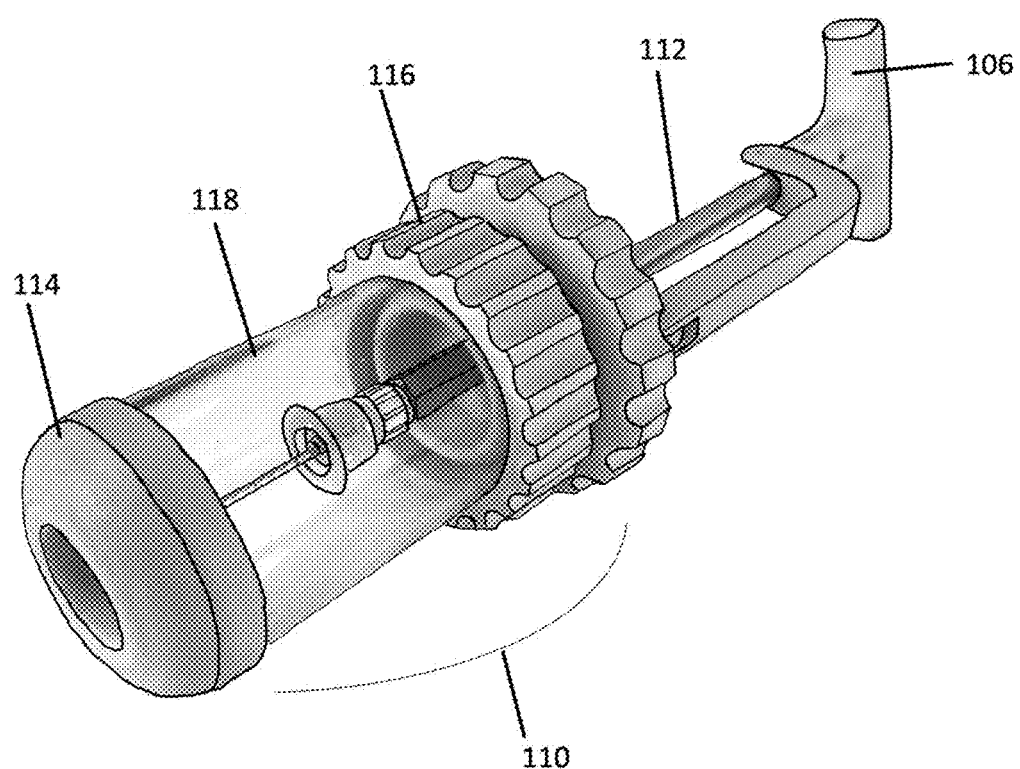
FIG. 1 is a perspective view of an IO device in accordance with a number of embodiments of the present disclosure.

The present disclosure pertains to devices and methods for the practice of intraosseous infusion for fluid and medication injection into the bone marrow. More particularly, the present disclosure relates to an intraosseous needle removal device and the method for safely extracting and disposing of the needle. Fluids and medication may be administered to patients by IO infusion when, for instance, intravenous infusion is not possible. This occurs, for example, when a patient's blood pressure has fallen such that their vessels have collapsed, preventing access. IO infusion, in contrast to intravenous infusion, uses the bone as a non-collapsible cavity for the introduction of fluids and medication. IO needles are commonly removed both in hospitals and morgues. As referred to herein, a user is a person who removes an IO needle from a body or disposes of an IO needle removed from a body. For example, a user can include a doctor, a medic, a nurse, a technician, and/or other people.

When the IO needle/cannula is to be removed, one current approach is to affix a standard medical syringe to the IO needle via a threaded connection. The syringe is then pulled or yanked, requiring significant force away from the patient body. While standard medical syringes may act as a handle for IO needle removal in this manner, they are not designed specifically for this purpose and lack desired characteristics for stable and manageable removal. This approach requires a strong and experienced individual to successfully dislodge the needle from the bone.

Following removal, the IO needle is immediately placed in a disposal container as is the standard practice for sharps disposal. When using a standard medical syringe for extraction, the needle is not shielded or protected between its removal from the patient and placement in a disposal container. This can result in accidental puncture of the patient or the professional if the energy required for the extraction cannot be controllably stopped at the moment of removal.

The present disclosure relates to a device and a method enabling safe removal of an IO needle from the body, protection from accidental puncture of the removed needle, and safe disposal of the needle following the procedure. The device also enables a wide range of users with varying degrees of strength to safely remove the needle from the body by providing balanced counterforces and eliminating the need to place the hand near the needle during the extraction. The device may be configured to be connected to an implanted IO needle and placed against the body. Additionally, the device may be configured to provide a surface area for stabilization from the user's non-dominant hand allowing the hand to remain away from the needle. The device may be configured to contain the removed needle and may be locked to prevent the reemergence of the needle from the device. In some embodiments, the needle may be safely decoupled from the device and disposed of, allowing the device to be cleaned and reused.

FIG. 1 is a perspective view of an IO device 100 in accordance with a number of embodiments of the present disclosure. FIG. 1 shows one embodiment of the device 100 in a retracted, locked position. An intraosseous device 100 may include the chamber 110, a tensile puller 112, and an actuator 106. The chamber 110 may include a skin engagement surface 114, an articulating surface 116, and a sidewall 118 which may connect the skin engagement surface 114 and articulating surface 116. The skin engagement surface 114 may be referred to herein as a first surface 114. The articulating surface 116 may be referred to herein as a second surface 116. The tensile puller 112 may slidingly connect with the second surface 116 of the chamber 110.

Figure 2:
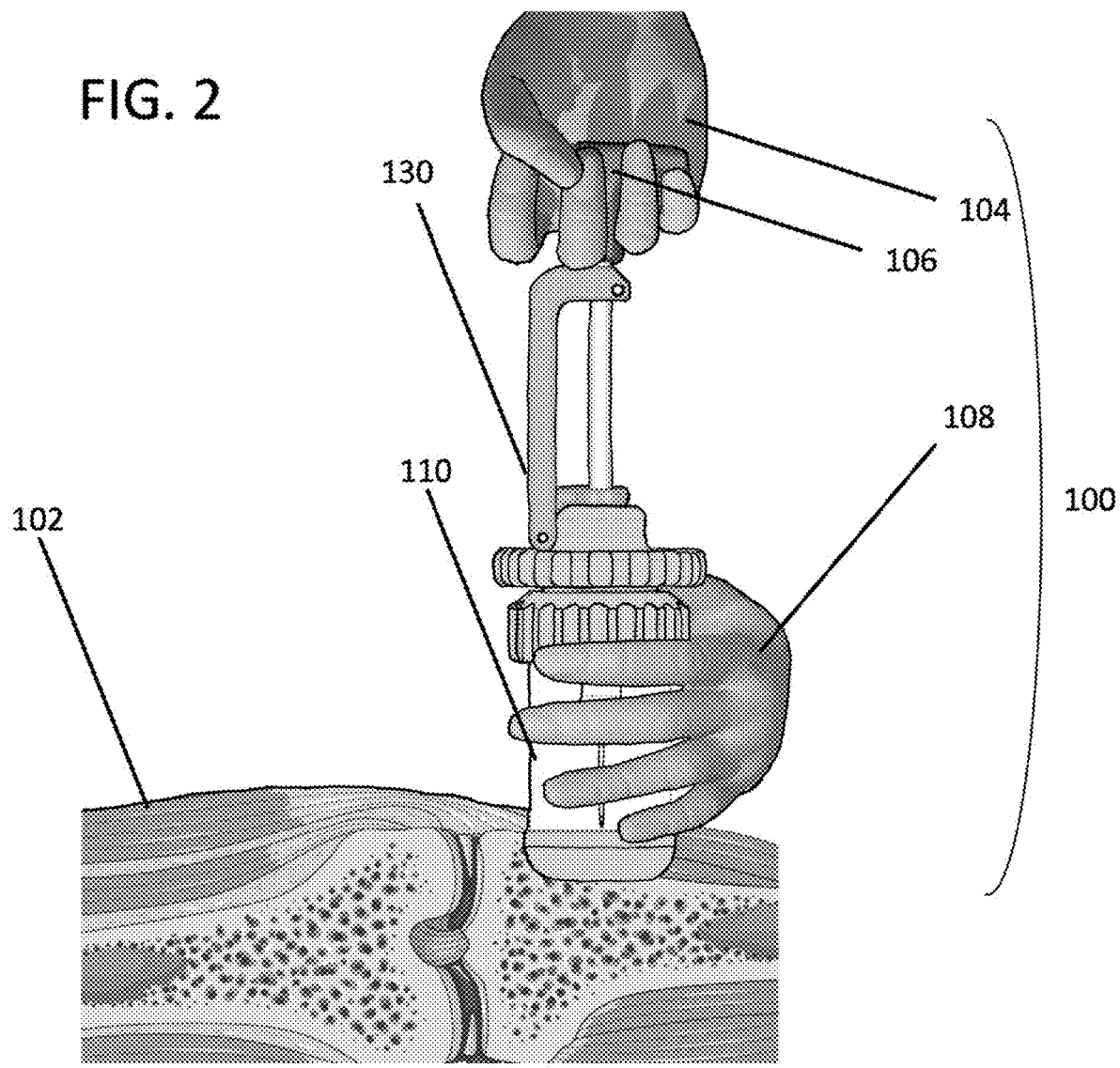
FIG. 2 is a side view of an IO device in operation in accordance with a number of embodiments of the present disclosure.

FIG. 2 is a side view of an IO device 100 in operation in accordance with a number of embodiments of the present disclosure. FIG. 2 shows one embodiment of the device 100 pressed against a patient body 102, having extracted the needle. The device 100 may be pressed against the patient body 102 where an IO needle has been inserted. The device 100 may be held with two hands, a dominant hand 104 providing force on the actuator 106 and a non-dominant hand 108 providing force on the chamber 110. Alternatively, the non-dominant hand 108 may provide the force on the actuator 106 and the dominant hand 104 may provide the force on the chamber 110. Application of force on the actuator 106 causes the device 100 to withdraw (e.g., pull) the needle out of the bone and up into the chamber 110. One or more locking mechanisms 130 may be engaged to prevent exposure of the needle. In some embodiments, the device 100 and the needle are discarded together. In some embodiments, the device 100 may be cleaned (e.g., disinfected or autoclaved) for another use upon separation of the needle from the device 100.

Figure 3:
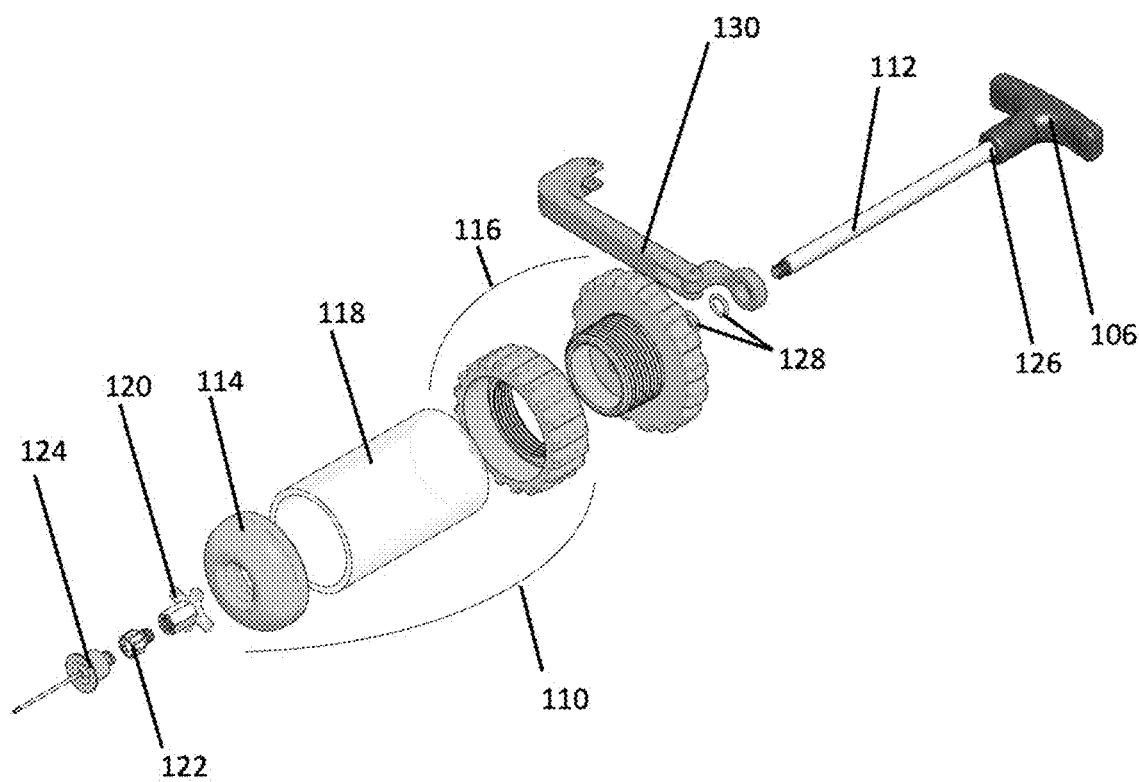
FIG. 3 is an exploded view of an IO device in accordance with a number of embodiments of the present disclosure.

FIG. 3 is an exploded view of an IO device 100 in accordance with a number of embodiments of the present disclosure. The chamber 110 may be comprised of the first surface 114, the sidewall 118, and the second surface 116. In some embodiments, the second surface 116 may be comprised of two or more separate, interlocking threaded pieces to allow for further disassembly of the device 100. An actuating end 120 of the tensile puller 112 may be threaded to removably pair with one or more connectors 122 and a needle 124. A proximal end 126 of the tensile puller 120 may connect to the actuator 106. The tensile puller 112 may slidingly connect to the second surface 116 and may be constricted by friction provided by one or more seals 128. One or more locking mechanisms 130 may slidingly connect with the tensile puller 112. Alternatively or additionally, one or more locking mechanisms 130 may be fixed to the tensile puller 112 or to the chamber 110.

Figure 4:
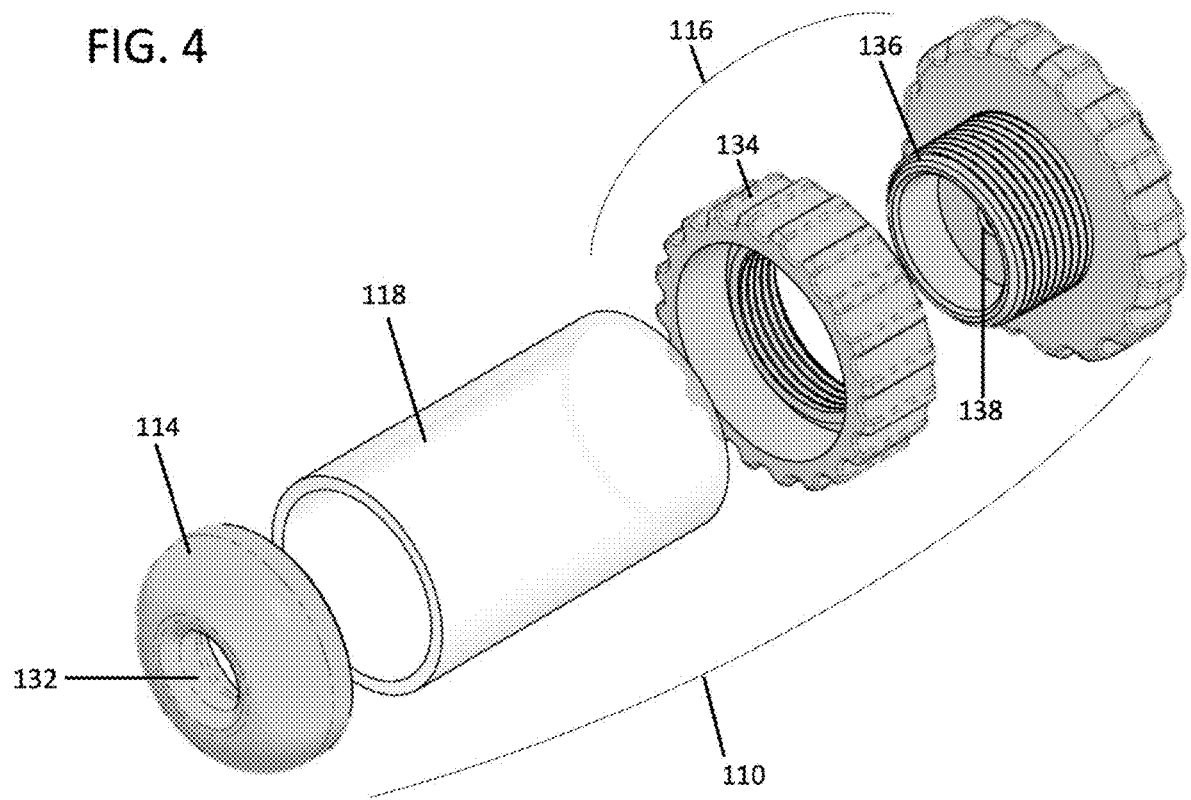
FIG. 4 is an exploded view of a chamber of an IO device in accordance with a number of embodiments of the present disclosure.

FIG. 4 is an exploded view of a chamber 110 of an IO device 100 in accordance with a number of embodiments of the present disclosure. FIG. 4 shows the parts which may comprise one embodiment of the chamber 110. The chamber 110 may house the extracted needle 124 and may be configured to be securely held by the non-dominant hand 108. Alternatively, the chamber 110 may be securely held by the dominant hand 104. The first surface 114 of the chamber 110 may have a first aperture 132. The first surface 114 may have a bullnose shape with rounded edges on the first aperture 132. The first surface 114 may be sized and shaped such as to contact a patient body 102 at various needle extraction points. The sidewall 118 may be at least partially transparent and may be fashioned in an ergonomic shape such as a cylinder, as shown in the example illustrated in FIG. 4. Alternatively or additionally, the sidewall 118 may be slotted such as to allow viewing into the chamber (e.g., in embodiments where the sidewall is not at least partially transparent). In some embodiments, the second surface 116 may be comprised of two or more interlocking threaded pieces which may removably pair. A removable component 134 of the second surface 116 may have exterior ridges and/or knurling and interior male or female threading. A receiving 136 component of the second surface 116 may also have exterior gripping teeth with a male or female threaded member for removably pairing with the removable component 134 of the second surface 116. The receiving component 136 of the second surface 116 may have a second aperture 138 which may be approximately the diameter of the tensile puller 112.

Figure 5:
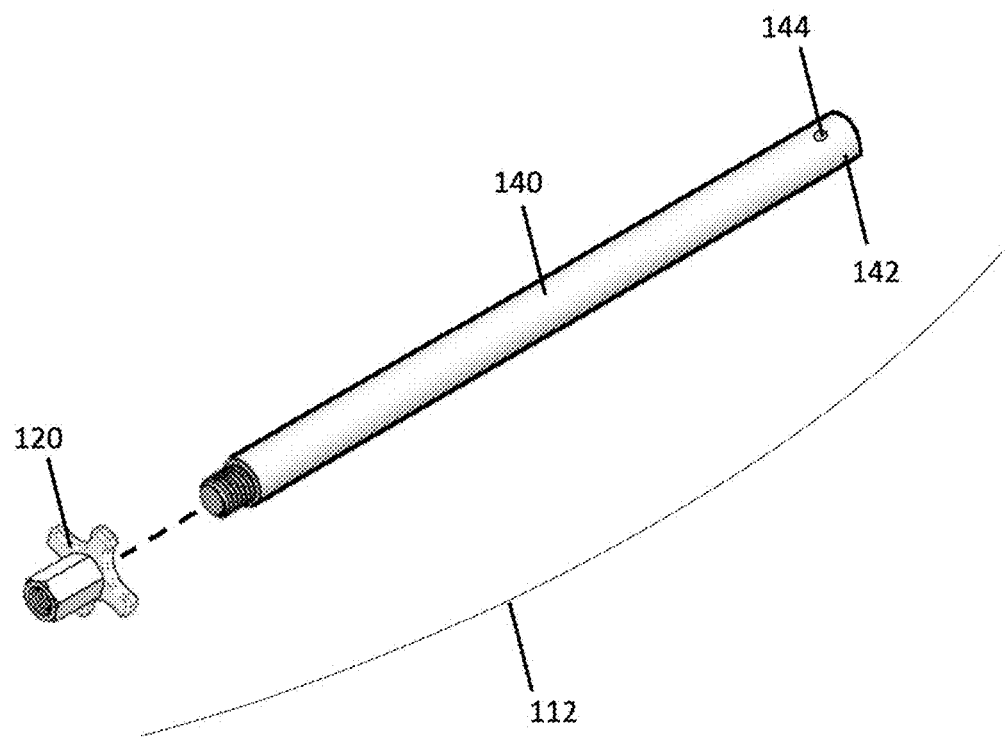
FIG. 5 is an exploded view of a tensile puller of an IO device in accordance with a number of embodiments of the present disclosure.

FIG. 5 is an exploded view of a tensile puller 112 of an IO device 100 in accordance with a number of embodiments of the present disclosure. FIG. 5 shows the parts which may be configured to form one embodiment of the tensile puller 112. The tensile puller 112 may enable the actuator 106 to exert tensile force on the needle 124. The tensile puller 112 may be comprised of a middle component 140 which may connect to the actuating end 120 of the tensile puller 112. The middle component 140 and actuating end 120 of the tensile puller 112 may be removably coupled by threading, as shown, or may be fixed together by a chemical bond, such as epoxy, acrylic glue, or cyanoacrylate, a bore and pin, a welded or soldered joint, or other connection. The coupling end 142 of the tensile puller 112 may be approximately equal to the inner diameter of the actuator 106 and may have a tensile puller bore 144 to allow for fixation to the actuator 106 with an actuator pin 148.

Figure 6:
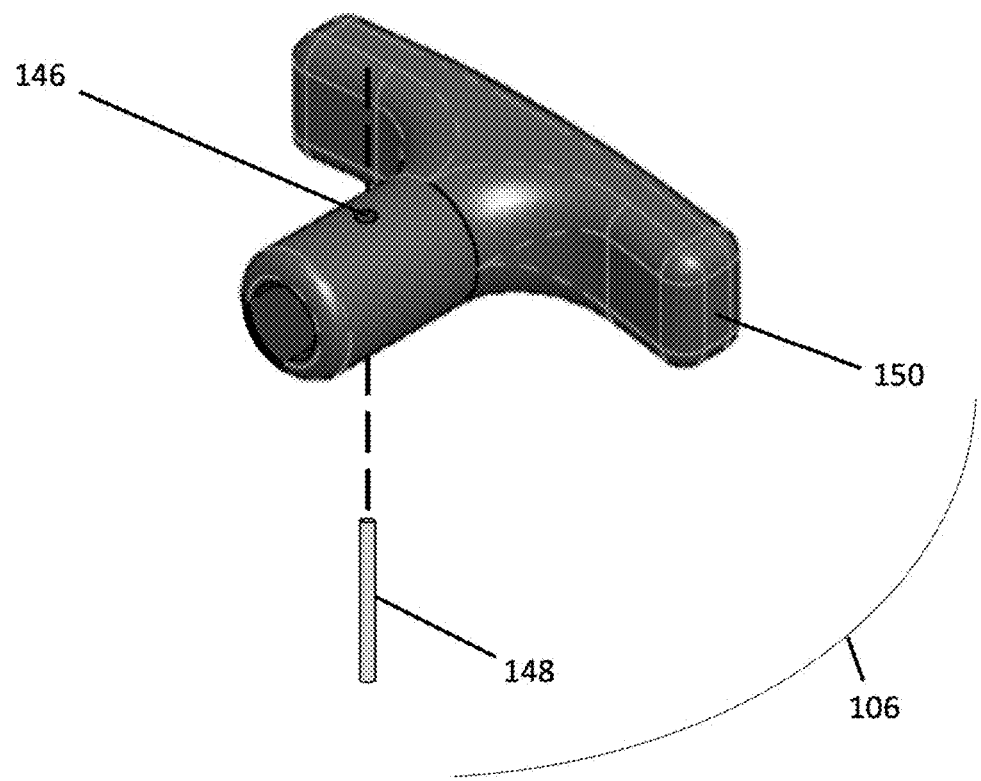
FIG. 6 is an exploded view of an actuator of an IO device in accordance with a number of embodiments of the present disclosure.

FIG. 6 is an exploded view of an actuator 106 of an IO device 100 in accordance with a number of embodiments of the present disclosure. The actuator 106 may enable the user to exert precise, controlled force on the tensile puller 112. The actuator 106 may have an actuator bore 146 through which an actuator pin 148 may be fixed in order to pair the actuator 106 to the coupling end of the tensile puller 142. Other methods of fixation may be used to pair the actuator 106 with the tensile puller 112. In some embodiments, the actuator 106 may be formed as a t-shaped handle 150. In another embodiment, the handle 150 may be ring-shaped. In yet another embodiment, the handle 150 may be hook-shaped. The actuator 106 may also be a mechanical trigger. The mechanical trigger may be positioned on a grip such as to allow for actuation by pulling the mechanical trigger with one or more fingers. The actuator 106 may also be electrically or pneumatically driven. The device 100 may include onboard electrical power or a pneumatic pressure source. The device 100 may be paired to a remote source of electrical power or pneumatic pressure.

Figure 7:
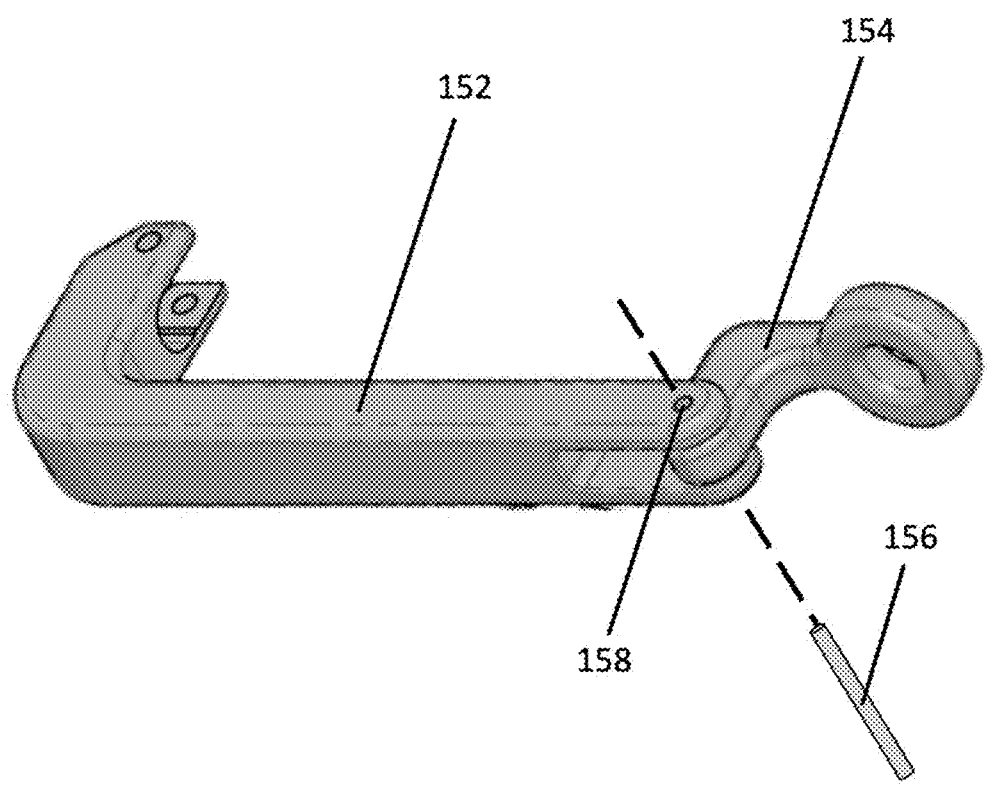
FIG. 7 is an exploded view of a locking mechanism of an IO device in accordance with a number of embodiments of the present disclosure.

FIG. 7 is an exploded view of a locking mechanism 130 of an IO device 100 in accordance with a number of embodiments of the present disclosure. FIG. 7 shows several parts which may comprise one embodiment of the locking mechanism 130. One or more locking mechanisms 130 may prevent the tensile puller 112 from moving back to a deployed position once it has been retracted, which may reduce the chance of accidental puncture by the needle 124. The locking mechanism 130 may be comprised of a locking shaft 152 which may hingedly connect to a locking fastening component 154. The locking shaft 152 may clamp to the tensile puller 112 near the second surface 116 of the chamber 110. The fastening component 154 may slidingly connect to the tensile puller 112. Alternatively, the fastening component 154 may be permanently fixed to the tensile puller 112. The shaft 152 may be of a length where, when clamped, the tensile puller 112 is braced by the shaft 152 and thus restricted from sliding motion in relation to the chamber 110. A locking mechanism pin 156 may be fixed through a locking mechanism bore 158 enabling hinging motion of the shaft 152 with respect to the fastening component 154.

Figure 8:
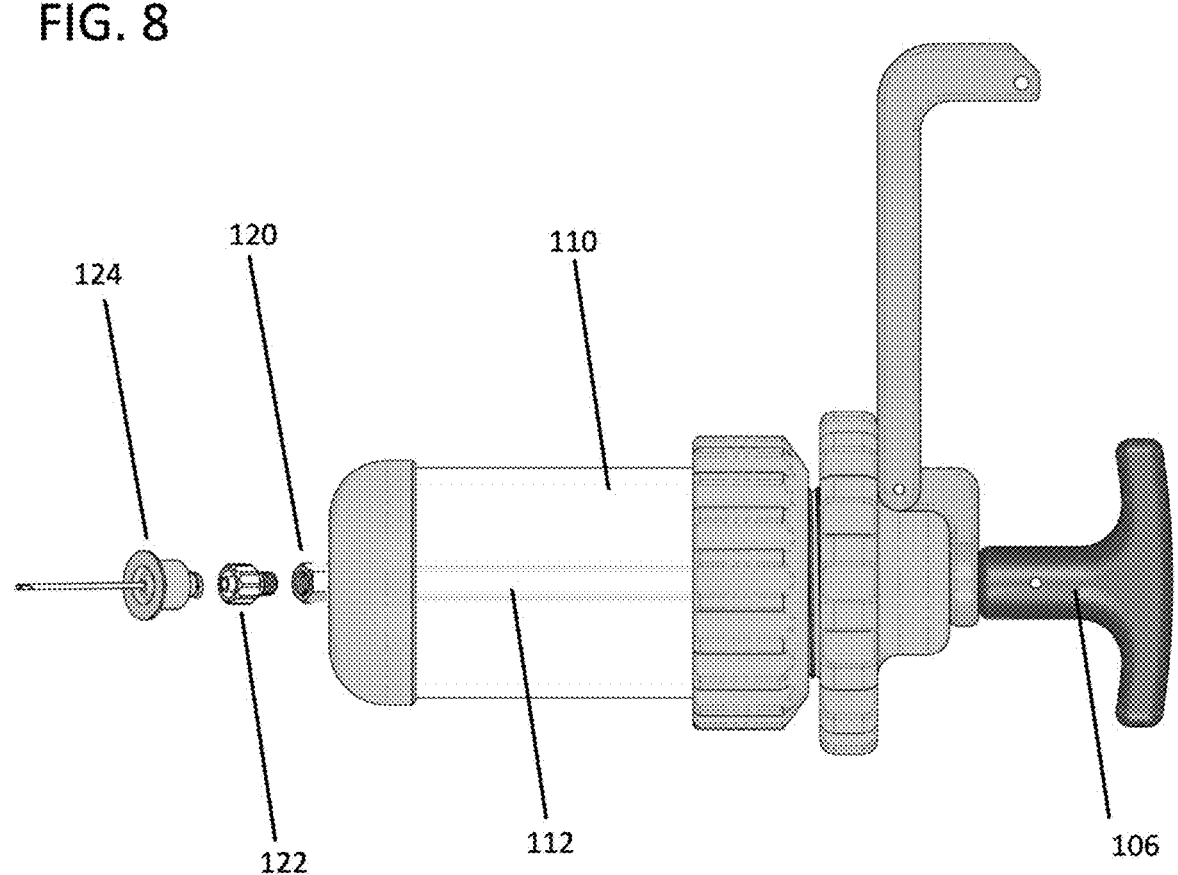
FIG. 8 is a side view of an unpaired IO device in accordance with a number of embodiments of the present disclosure.

FIG. 8 is a side view of an unpaired IO device 100 in accordance with a number of embodiments of the present disclosure. FIG. 8 shows one embodiment of the device 100 unlocked with the tensile puller 112 in a deployed position available for coupling with one or more connectors 122 and the needle 124. The actuating end 120 of the tensile puller 112 may protrude out of the first aperture 132 for ease and visibility of coupling. The actuating end 120 of the tensile puller 112 may be inner threaded to receive a male external threading of a connector 122. Alternatively, the actuating end 120 of the tensile puller 112 may be outer threaded to pair to a female inner threading of a connector. To the actuating end 120 of the tensile puller 112 may be attached a rotatable swivel nut with inner threading to receive the external threading of a mating piece such as a female Luer-Lock part. The actuating end 120 of the tensile puller 112 may be configured to couple interchangeably with one or more mating adapters configured to receive mating pieces of one or more connectors 122. The tensile puller 112 and actuator 106 may be rotated independently from the chamber 110 such as to allow for ease of coupling with the connector 122 and needle 124.

Figure 9:
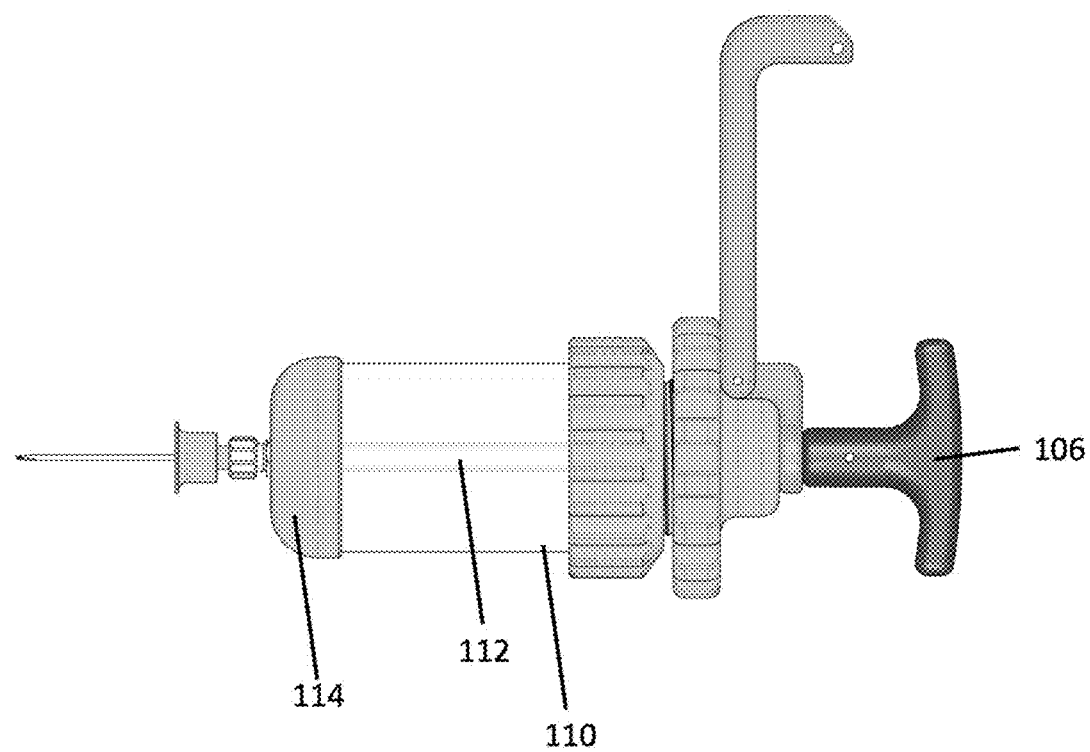
FIG. 9 is a side view of a paired IO device in accordance with a number of embodiments of the present disclosure.

FIG. 9 is a side view of a paired IO device 100 in accordance with a number of embodiments of the present disclosure. FIG. 9 shows one embodiment of the paired, unlocked device 100 with the tensile puller 112 in the deployed position. The device 100 may be configured to be held with the non-dominant hand 108 securing the chamber 110, pressing the first surface 114 against the patient body 102 and the dominant hand 104 gripping the actuator 106. Alternatively, the dominant hand 104 may secure the chamber 110 and non-dominant hand 108 may grip the actuator 106. In one embodiment, force on a handle-shaped actuator 106 away from the body, paired with a counterforce on chamber 110 towards the body causes the tensile puller 112 to move from the deployed position to the retracted position relative to the chamber 110, pulling the needle from the patient body 102 into the chamber 110. The device may be configured such that the force on the handle-shaped actuator 106 may encounter the counterforce on the chamber 110 physically within the device, such as to cause rapid deceleration of both forces in each of their respective directions.

Figure 10:
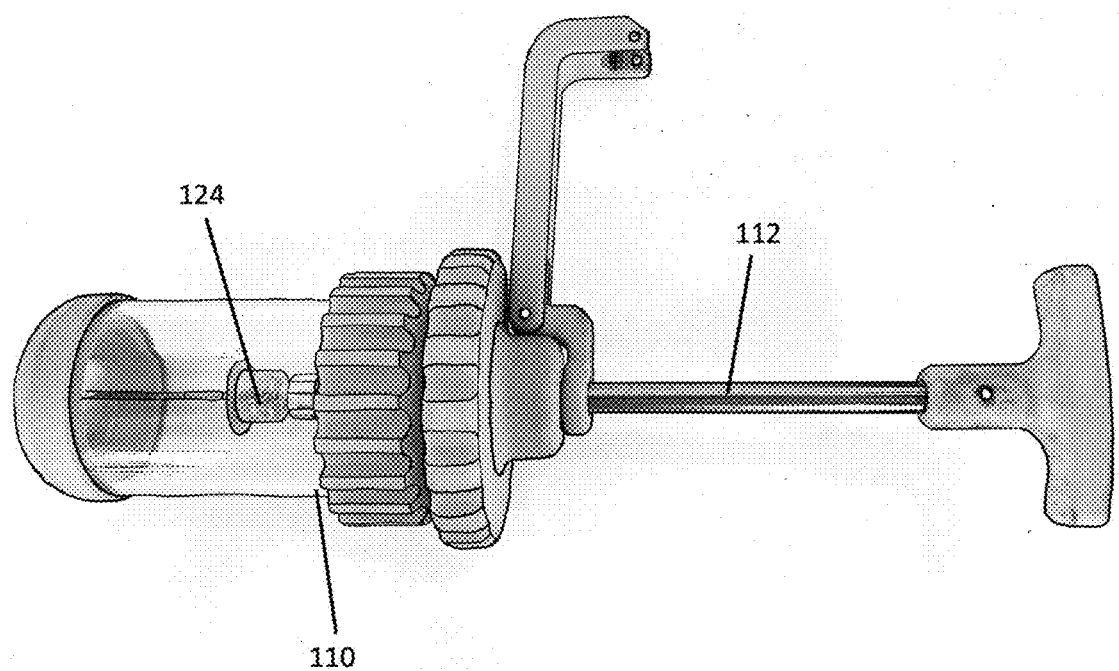
FIG. 10 is a side view of a retracted IO device in accordance with a number of embodiments of the present disclosure.

FIG. 10 is a side view of a retracted IO device 100 in accordance with a number of embodiments of the present disclosure. FIG. 10 depicts one embodiment of the unlocked device 100 with the tensile puller 112 in the retracted position. As shown in FIG. 10, a business end of the needle 124 is withdrawn past the front surface of the chamber 110, so as to prevent accidental puncture after removal or contamination from patient body fluids.

Figure 11:
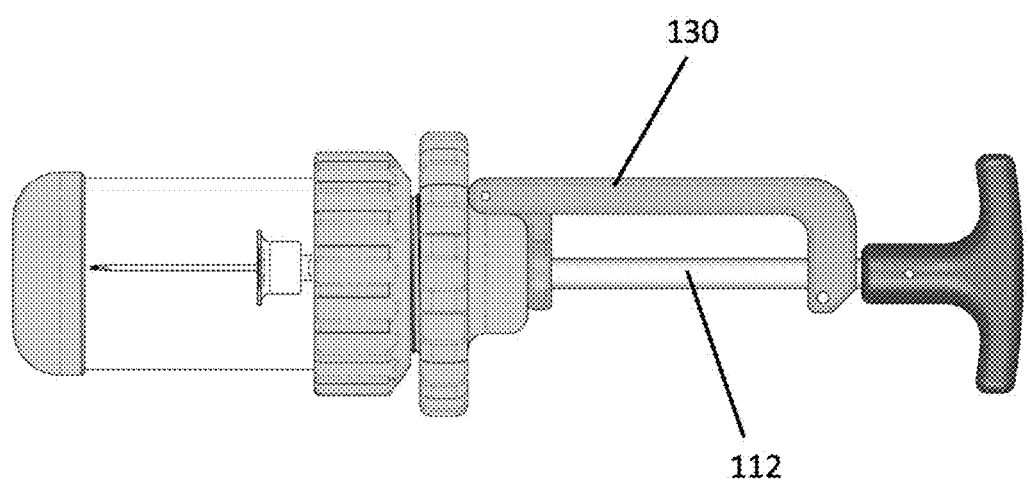
FIG. 11 is a side view of a retracted, locked IO device in accordance with a number of embodiments of the present disclosure.

FIG. 11 is a side view of a retracted, locked IO device 100 in accordance with a number of embodiments of the present disclosure. FIG. 11 shows one embodiment of the device 100 with the tensile puller 112 in the retracted position and with one or more locking mechanisms 130 engaged.

Figure 12:
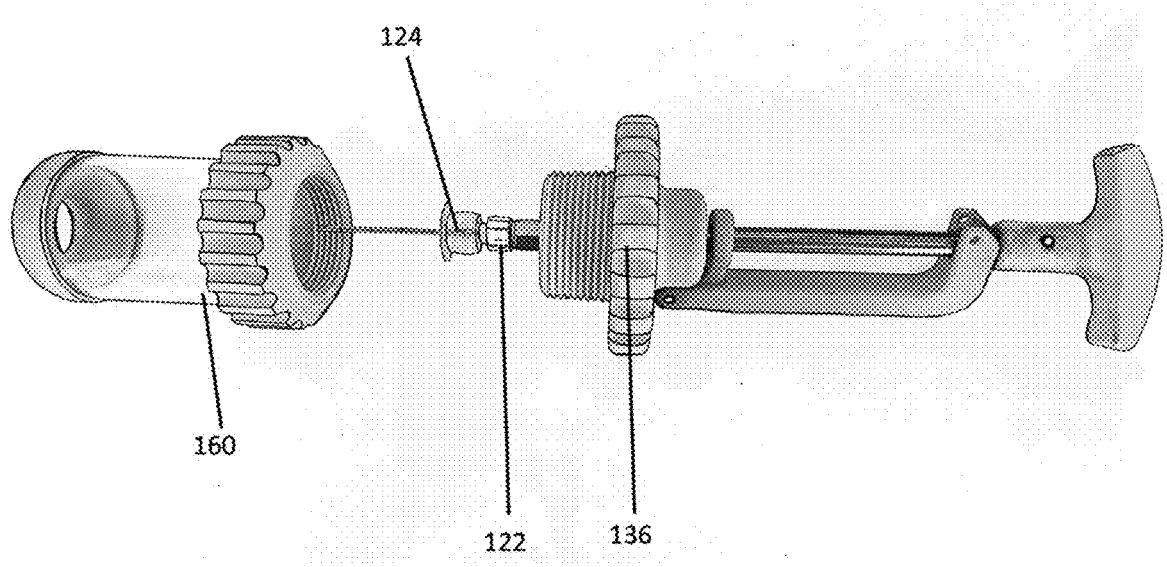
FIG. 12 is a side view of an IO device with an uncoupled chamber in accordance with a number of embodiments of the present disclosure.

FIG. 12 is a side view of an IO device 100 with an uncoupled chamber 110 in accordance with a number of embodiments of the present disclosure. One embodiment of the device 100 may be disassembled and the needle 124 and one or more connectors 122 unpaired from the actuating end 120 of the tensile puller 112. FIG. 12 shows one embodiment of the device 100 with a chamber module 160 unpaired from the receiving component 136 of the second surface 116 such as to expose the needle 124 and one or more connectors 122.

Figure 13:
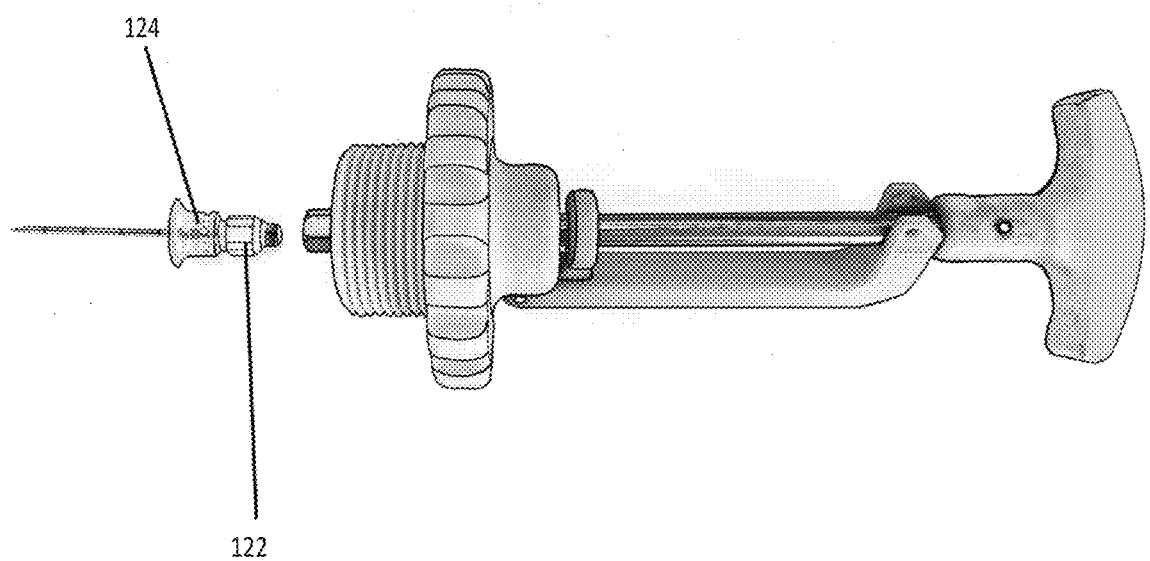
FIG. 13 is a side view of an IO device with a removed needle in accordance with a number of embodiments of the present disclosure.

FIG. 13 is a side view of an IO device 100 with a removed needle in accordance with a number of embodiments of the present disclosure. FIG. 13 shows one embodiment of the device 100 where the needle 124 and one or more connectors 122 have been unpaired from the device 100 for disposal.

In operation and use, a device 100 of the present disclosure may provide for safe removal of an implanted intraosseous needle by users of minimal strength or experience. In particular, a user may move a tensile puller 112 to the deployed position, as depicted in FIG. 8, for coupling with a needle 124 inserted in a patient body 102 and one or more connectors 122. In one embodiment, a user may rotate a t-shaped handle 150 to thread the actuating end 120 of the tensile puller 112 to one or more connectors 122 and the needle 124. A user may hold the chamber 110 with their non-dominant hand 108 and an actuator 106 with their dominant hand 104 while pressing the first surface 114 of the chamber 110 adjacent to the patient body 102. Force may be applied on an actuator 106 from the dominant hand 104, moving the tensile puller 112 from the deployed position, depicted in FIG. 9 to the retracted position depicted in FIG. 10. It should be understood here and throughout this entire disclosure that either hand may grip the device at either location. In applying force on the actuator 106 and moving the tensile puller 112 to the retracted position, the needle will be removed from the body and housed in the chamber 110. One or more locking mechanisms 130 may be configured to prevent the tensile puller 112 from reverting to the deployed position, exposing the extracted needle 124. In one embodiment, a chamber module 160 may then be configured to uncouple from the receiving component 136 of the second surface 116, allowing the needle 124 and one or more connectors 122 to be uncoupled from the actuating end 120 of the tensile puller 112 and disposed of. In some embodiments, the device 100 may be autoclaved or sanitized for subsequent use. In some embodiments, the needle 124 and one or more connectors 122 may remain coupled to the device 100 following extraction and one or more locking mechanisms 130 may be engaged. The locked, coupled device 100 may then be disposed of FIG. 14 is a diagram of a general overview of use of an IO device 100 in accordance with a number of embodiments of the present disclosure.

Figure 14:
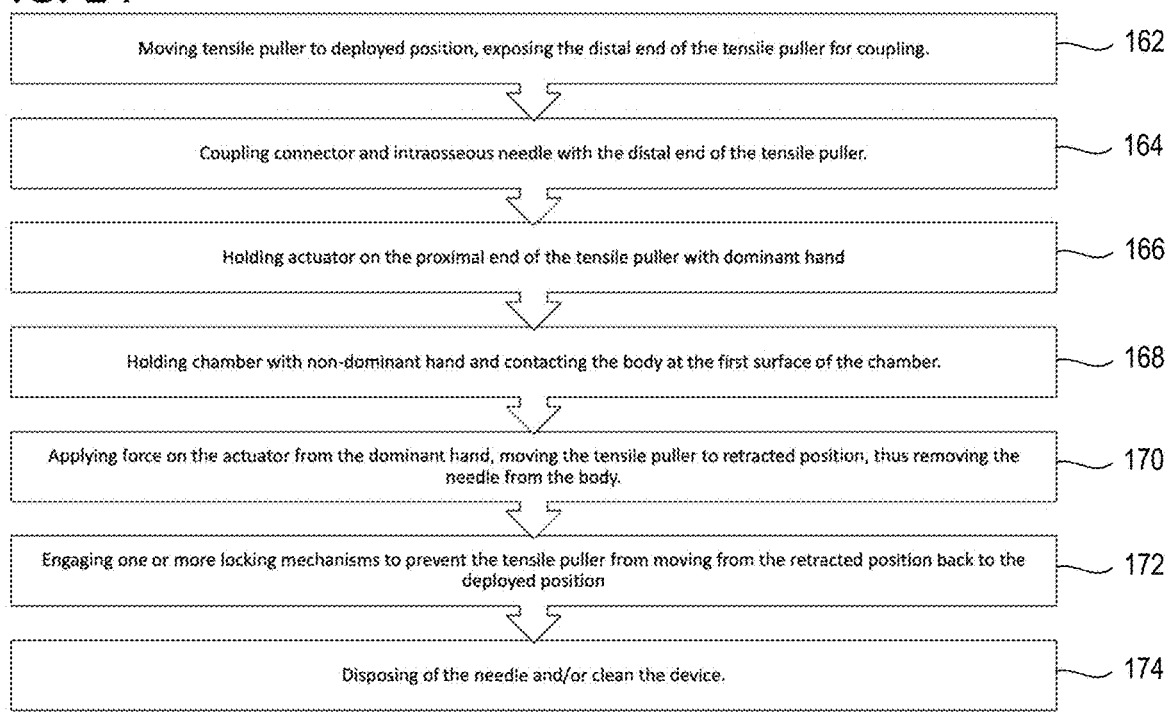
FIG. 14 illustrates a method of using an IO device in accordance with a number of embodiments of the present disclosure.

FIG. 14 illustrates a method of using an IO device in accordance with a number of embodiments of the present disclosure. At 162, the method includes moving the tensile puller to the deployed position, exposing the actuating end 120 of the tensile puller 112 for coupling. At 164, the method includes coupling the connector and intraosseous needle with the actuating end 120 of the tensile puller 112. At 166, the method includes holding the actuator 106 on the proximal end with the dominant hand. At 168, the method includes holding the chamber 110 with the non-dominant hand and contacting the patient body 102 at the first surface 114 of the chamber 110. At 170, the method includes applying force on the actuator 106 from the dominant hand, moving the tensile puller 112 to the retracted position, thus removing the needle 124 from the patient body 102. At 172, the method includes engaging one or more locking mechanisms 130 to prevent the tensile puller 112 from moving from the retracted position back to the deployed position. At 174, the method includes disposing of the needle 124 and/or cleaning the device. It is noted that embodiments herein are not so limited. For instance, alternatively, the device 100 may remain paired to the needle 124 and be disposed therewith.

Figure 15A:
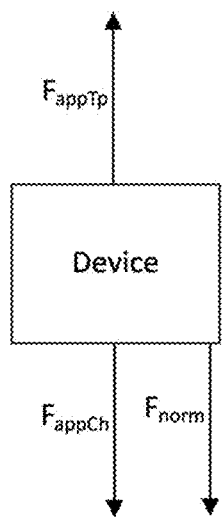
FIG. 15A is a diagram of forces implicating an IO device in accordance with a number of embodiments of the present disclosure.
Figure 15B:
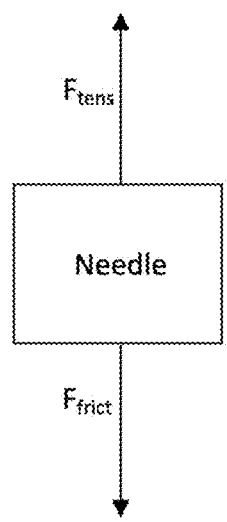
FIG. 15B is a diagram of forces implicating an IO device in accordance with a number of embodiments of the present disclosure.
Figure 15C:
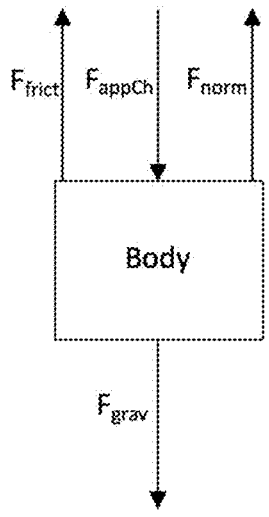
FIG. 15C is a diagram of forces implicating an IO device in accordance with a number of embodiments o the present disclosure.

FIGS. 15A-15C illustrate forces implicating an IO device 100 in accordance with a number of embodiments of the present disclosure. FIGS. 15A-15C show free body diagrams illustrating the relevant forces on the device 100, the needle 124, and the patient body 102; respectively. The device 100 may be sized and shaped such as to allow use of the device without the need for the user to place either hand directly on the patient body 102. As such, the device may allow the user to utilize a technique that places insubstantial excess force on the patient body 102 (depicted in FIG. 15C as $F_{appCh}$). The applied force on the tensile puller 112 ($F_{appTp}$) may also be directly or substantially opposing the patient body's 102 gravitational force ($F_{grav}$), further reducing the need for a substantial excess applied counterforce on the chamber 110 ($F_{appCh}$). The reduced $F_{appCh}$ may provide for less pressure from the device on the patient body 102 during the procedure such as to minimize discomfort.

The device 100 may also be configured to facilitate the collision of multiple counterforces within the device, such as to minimize inadvertent or unnecessary movement from the user during the procedure. The force applied to the tensile puller 112 ($F_{appTp}$) may oppose a counterforce applied to the chamber 110 ($F_{appCh}$). Following the sliding action of the tensile puller 112 moving through the chamber 110, the actuating end 120 of the tensile puller 112 may collide with the second surface 116 of the chamber 110. Consequently, this collision will overcome the respective inertias of both $F_{appTp}$ and $F_{appCh}$. The lack of extraneous substantial inertia of any forces involved in using the device 110 after the needle 124 has been dislodged from the bone may allow for better control and safety in the procedure.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including"

and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An intraosseous device, comprising:
   a chamber portion having a proximal end and a distal end, wherein the proximal end includes a base comprising a receiving component and a removable component;
   a tensile puller extending through the chamber portion and slidingly engaging the receiving component, the tensile puller comprising a continuous member extending from a proximal end to a distal end;
   a laterally extending handle configured for pulling the tensile puller and a needle from a bone, the laterally extending handle being arranged on the proximal end of the tensile puller and defining a proximal most end of the intraosseous device;
   a connector on the distal end of the tensile puller adapted to engage the needle; and
   a lock arranged on the chamber portion and configured to directly engage with the tensile puller.

2. The device of claim 1, wherein the chamber portion includes a first surface including a first aperture, a second surface including a second aperture, and a sidewall connecting the first surface to the second surface.

3. The device of claim 2, wherein the tensile puller is configured to rotate independently from the chamber portion and is frictionally held by a seal around the tensile puller in the second aperture.

4. The device of claim 2, wherein the tensile puller is configured to alternate between:
   a deployed position, wherein the tensile puller is positioned such that the connector is at least partially within the first aperture; and
   a retracted position wherein the tensile puller is positioned such that the connector and the needle are encircled by the sidewall.

5. The device of claim 4, wherein the device further comprises an actuating end connecting the tensile puller to the connector.

6. The device of claim 2, wherein the first surface is constructed of a material suitable for contacting skin.

7. The device of claim 2, wherein the first surface comprises a bullnose shape adapted to contact a patient body.

8. The device of claim 2, wherein the sidewall is cylindrical in shape.

9. The device of claim 2, wherein the first surface and sidewall are removably connected by a threading to the second surface of the chamber for disassembly.

10. The device of claim 1, wherein the device includes an engaging means for connecting the tensile puller to the connector.

11. The device of claim 1, wherein the lock prevents the tensile puller from moving to a deployed position while in a retracted position.

12. The device of claim 1, wherein the device is configured to provide a distribution of forces where a force of actuation of the tensile puller is between the device and a patient body.

13. The device of claim 1, wherein the chamber portion is at least partially transparent.

14. The device of claim 1, wherein the lock is pivotally coupled to the chamber portion.

15. A method for extracting an intraosseous needle from a patient comprising:
   providing a medical device comprising a chamber, a tensile puller, a laterally extending handle, a connector, and a lock configured to directly engage the tensile puller, wherein the chamber comprises a base with a receiving component and a removable component;
   coupling the needle to the connector on a distal end of the tensile puller;
   applying a force to the chamber towards a distal end of the chamber such that the distal end of the chamber contacts a patient body; and
   applying an opposing force to the laterally extending handle on a proximal end of the tensile puller, the opposing force effectively altering the tensile puller from a deployed position to a retracted position by sliding relative to the receiving component.

16. The method of claim 15, further comprising engaging the lock to prevent the tensile puller from returning to the deployed position from the retracted position.

17. The method of claim 15, wherein the method includes applying a rotational force using the tensile puller.

18. The method of claim 15, wherein the method includes disposing of the device subsequent to altering the tensile puller from the deployed position to the retracted position.

19. The method of claim 15, wherein the method includes disposing of the needle, and wherein disposing of the needle comprises:
   disassembling the chamber;

decoupling the needle from the connector at the distal end of the tensile puller; and autoclaving the device.

20. The method of claim 15, wherein the method includes applying the opposing force to the laterally extending handle until the needle coupled to the connector is withdrawn into the chamber.

* * * * *